United States Patent [19]

Riccio et al.

[11] Patent Number: 5,759,530
[45] Date of Patent: Jun. 2, 1998

[54] COMPOSITION AND METHOD OF PREPARING MICROEMULSION BLENDS

[75] Inventors: Donna A. Riccio, Watervliet; James H. Merrifield, Ballston Spa, both of N.Y.

[73] Assignee: General Electric Company, Waterford, N.Y.

[21] Appl. No.: 631,752

[22] Filed: Apr. 10, 1996

Related U.S. Application Data

[62] Division of Ser. No. 221,151, Mar. 31, 1994, Pat. No. 5,518,716.

[51] Int. Cl.$^6$ .................................... A61K 9/107
[52] U.S. Cl. ................ 424/70.12; 424/401; 424/70.121; 514/938
[58] Field of Search ............... 424/401, 70, 121; 514/938–943

[56] References Cited

U.S. PATENT DOCUMENTS

| | | | |
|---|---|---|---|
| 4,247,330 | 1/1981 | Sanders, Jr. ................... | 106/3 |
| 4,620,878 | 11/1986 | Gee ........................ | 106/287.15 |
| 4,705,704 | 11/1987 | Lane et al. .................. | 427/389.9 |
| 4,733,677 | 3/1988 | Gee et al. ................... | 132/207 |
| 4,782,095 | 11/1988 | Gum ........................ | 514/772 |
| 4,797,272 | 1/1989 | Linn ........................ | 424/59 |
| 4,801,447 | 1/1989 | Gum ........................ | 424/68 |
| 4,824,877 | 4/1989 | Glover et al. ............... | 523/221 |
| 4,842,766 | 6/1989 | Blehm et al. ................ | 252/309 |
| 4,999,398 | 3/1991 | Graiver et al. ............... | 524/837 |
| 5,057,572 | 10/1991 | Chrobaczek et al. .......... | 524/588 |
| 5,132,443 | 7/1992 | Traver ...................... | 556/425 |

*Primary Examiner*—Jyothsan Venkat
*Attorney, Agent, or Firm*—Kenneth S. Wheelock

[57] ABSTRACT

A microemulsion composition comprising a microemulsifiable silicone and a volatile silicone, the microemulsion formed therewith, a means for preparing said microemulsion, and personal care products comprising said microemulsion.

5 Claims, No Drawings

COMPOSITION AND METHOD OF PREPARING MICROEMULSION BLENDS

This is a divisional of co-pending application Ser. No. 08/221,151 filed on Mar. 31, 1994, now a U.S. Pat. No. 5,518,718.

FIELD OF THE INVENTION

The instant invention comprises a microemulsion comprising a blend of a silicone that readily forms a microemulsion with one or more volatile silicones and a method for preparing said microemulsion. The instant invention further comprises personal care products comprising said microemulsion blend.

BACKGROUND OF THE INVENTION

The instant invention is related to a composition and method of making microemulsion blends having an average particle size of from about 0.001 microns to about 0.05 microns whereby the blend comprises at least one volatile silicone and a silicone capable of forming microemulsions. The instant invention is further related to personal care products comprising said microemulsion blends comprising one or more volatile silicones.

Microemulsions containing silicone fluids have been found to be useful in a variety of personal care products such as hair conditioners and other cosmetic formulations. As defined herein, the term "microemulsions" refers to transparent, mechanically and thermally stable systems comprising small droplets having a mean or average particle diameter usually not more than 0.05 microns in diameter, preferably not more than 0.040 microns in diameter and most preferably not more than 0.025 microns in diameter. The small size of the droplets imparts a high degree of transparency to the emulsion. Cosmetic formulations containing microemulsions possess improved aesthetic values as well as improved physical properties.

The use of microemulsions in cosmetic applications is known in the art, see for example U. S. Pat. Nos. 4,797,272 (Linn et al.) and 4,620,878 (Gee). U.S. Pat. No. 4,797,272 to Linn et al. discloses water-in-oil microemulsion compositions having a mean droplet size ranging from about 0.001 microns to about 0.200 microns and containing moisturizers or sunscreens, surfactants, oils (e.g. cyclic dimethyl polysiloxanes), and skin humectants. U.S. Pat. No. 4,620,878 to Gee discloses a polyorganosiloxane emulsion that contains a polyorganosiloxane containing at least one polar radical such as an amino radical attached to the silicon of the siloxane by Si—C or Si—O—C bonds or at least one silanol radical and a surfactant that is insoluble in the polyorganosiloxane. The emulsion prepared by Gee has an average particle size of less than 0.14 microns and can be prepared by forming a translucent oil concentrate by mixing the polyorganosiloxane, at least one surfactant, and water and then forming a polyorganosiloxane emulsion of the oil-in-water type by rapidly dispersing the translucent oil concentrate in water.

Microemulsions of volatile silicones are taught in the art, for example U.S. Pat. Nos. 4,782,095 and 4,801,447, however these microemulsions have required large amounts of surfactants. The high levels of surfactants required in the prior art applications are detrimental in many applications. For example, in hair conditioners, such high surfactant levels lead to excessive foaming and poor tactile properties.

While microemulsions of aminofunctional silicones provide beneficial conditioning results when applied to damaged hair tresses they provide little benefit in wet combing. In contrast, volatile silicones provide excellent wet combing properties. It continues to be desirable to provide alternative or improved methods for preparing microemulsion blends of small average particle size that comprise volatile silicones.

SUMMARY OF THE INVENTION

In one embodiment, the instant invention comprises a transparent oil-in-water microemulsion comprising: (a) a microemulsifiable silicone, (b) a volatile silicone, (c) a surfactant, and (d) water.

In another aspect, the instant invention provides a method of preparing a transparent polyorganosiloxane microemulsion having a mean particle size of from about 0.001 to about 0.050 microns, preferably from about 0.010 to about 0.030 microns, and most preferably from about 0.010 to about 0.025 microns, comprising a microemulsifiable silicone and at least one volatile silicone.

Other aspects of the invention are microemulsions of polydimethylsiloxane, polymethylmethacrylates and the like, cosmetic formulations, especially shampoos, involving the microemulsion blends of the amino-functional polyorganosiloxane microemulsions and oligomeric organosiloxanes, and the like.

DETAILED DESCRIPTION OF THE INVENTION

The instant invention is based upon the discovery that functionalized silicones such as amino functional silicones which are capable of forming microemulsions may be blended with volatile silicones such as octamethylcyclotetrasiloxane and decamethylcyclopentasiloxane and the blend processed such that the mixture of silicones also forms a microemulsion. Such microemulsions are generally transparent. By transparent applicants mean the absence of turbidity or haze wherein haze is defined by an ASTM test, specifically ASTM test number D871 using turbidity suspension standards and wherein said haze or turbidity is below an upper limit of about 150. At levels of the haze number above about 50 the microemulsions of the present invention begin to gradually change from transparent to translucent. The haze numbers of the microemulsions of the present invention range from 0 to about 150, more preferably from about 0 to about 80 and most preferably from 0 to about 50. The turbidity suspension standards used in the ASTM test D871 are available from Hellige Incorporated of Garden City, N. Y. Applicants note that pure distilled water is 0 on the haze scale.

Polyorganosiloxane microemulsions prepared by the method of the instant invention have a mean particle size of from about 0.005 to about 0.050 microns, preferably from about 0.010 to about 0.030 microns, and most preferably from about 0.010 to about 0.025 microns. Generally haze and average particle size correlate with one another but they are also affected by the relative amounts of the two major components of the emulsion, the silicone oil and the water. Thus while at a constant oil to water ratio the haze and average particle size might correlate, haze by itself is not both a necessary and sufficient criterion to be an indicator of average particle size in a microemulsion unless other constraints are specified.

By microemulsifiable applicants define the term to mean capable of forming a microemulsion wherein the mean particle size of the emulsion ranges from 0.0001 microns to about 0.050 microns. By microemulsifiable silicone applicants define a silicone or a mixture of silicones that can form a microemulsion as defined by applicants hereinbefore. Volatile silicones, as hereinafter defined, are not by themselves intrinsically members of the class of microemulsifiable silicones, although when mixed with a microemulsifiable silicone they may then comprise part of a microemulsifiable silicone mixture.

In step the method of the instant invention an oil surfactant mixture is prepared by blending:

(1) an amount ranging from 10 to 30 parts per hundred of the final composition of the microemulsion of a polyorganosiloxane that can be microemulsified, A(1), optionally having an amino content of from about 0.6 to about 3.0 milliequivalents per gram and comprising a silicone of the formula:

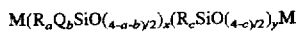

whereby in the formulas above R is a hydrocarbon or hydrocarbon radical having from 1 to about 6 carbon atoms, Q is a polar radical having the general formula —$R^1HZ$, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals containing from 1 to 4 carbon atoms, and —$CH_2CH_2NH_2$ radicals; "a" assumes values ranging from about 1 to about 2, "b" assumes values ranging from about 1 to about 3, "a"+"b" is less than or equal to 3, and "c" is a number in the range of from about 1 to about 3; and x is a number in the range of from 1 to about 20 preferably from about 1 to 10 and most preferably about 8, and y is a number in the range from about 20 to about 800, preferably from about 100 to about 500, and most preferably about 275, and M is any suitable silicone endstopping group known in the art. Non-limiting examples of radicals represented by R include alkyl radicals such as methyl, ethyl, propyl, isopropyl, butyl, isobutyl, amyl, isoamyl, hexyl, isohexyl, and the like; alkenyl radicals such as vinyl, halo vinyl, alkyl vinyl, allyl, haloallyl, alkylallyl, cycloalkyl radicals such as cyclobutyl, cyclopentyl, cyclohexyl and the like, phenyl radicals, benzylradicals, halohydrocarbon radicals such as 3-chloropropyl, 4-bromobutyl, 3,3,3-trifluoropropyl, chlorocyclohexyl, bromophenyl, chlorophenyl and the like, and sulfur containing radicals such as mercaptoethyl, mercaptopropyl, mercaptohexyl, mercaptophenyl and the like; preferably R is an alkyl radical containing from 1 to about 6 carbon atoms; and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, $OCH_2CH_2$—, —$OCH_2CH_2CH_2$—, —$CH_2CH(CH_3)C(O)OCH_2$, $(CH_2)_3CC(O)OCH_2CH_2$—, —$C_6H_4C_6H_4$—, —$C_6H_4CH_2C_6H_4$—, and $(CH_2)_3C(O)SCH_2CH_2$—.

Z is most preferably a —$CH_2CH_2NH_2$ radical.

Q is most preferably an amine functional polar radical having the formula —$CH_2CH_2CH_2NHCH_2CH_2NH_2$.

In the formulas, "a" assumes values ranging from about 1 to about 2, "b" assumes values ranging from about 1 to about 3, "a"+"b" is less than or equal to 3, and "c" is a number in the range of from about 1 to about 3. The molar ratio of $R_aQ_bSiO_{(4-a-b)/2}$ units to $R_cSiO_{(4-c)/2}$ units ranges from about 1:2 to about 1:65, preferably from about 1:5 to about 1:65, and most preferably from about 1:15 to about 1:20.

When it is preferred to use amino functional silicone fluids A(1) in the instant invention the preferred fluids have the formula:

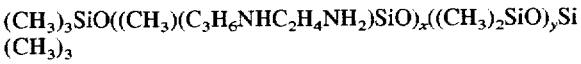

wherein x is a number in the range of from 1 to about 20 preferably from about 1 to 10 and most preferably about 8, and y is a number in the range from about 20 to about 800, preferably from about 100 to about 500, and most preferably about 275.

(2) from about 0.5 to about 25 parts per hundred of the final composition of the microemulsion of a volatile silicone, A(2), of the formula:

here $R_d$ and $R_e$ may be identical or different and are selected from the group of alkyl radicals containing from 1 to 4 carbon atoms and where n is an integer varying from between about 3 to about 7.

(3) adding to the silicone blend from step (1), of from about 1 to 20 parts per hundred of the final composition of the microemulsion of at least one surfactant, A(3), wherein at least one of the surfactants is insoluble in the polyorganosiloxane;

(4) heating the blend of silicones and surfactant(s) to a temperature ranging from 35° to 90° C. while stirring;

(5) water, Part I water in the examples, in the amount of from about 0.50 to about 5.00 parts per hundred of the final composition of the microemulsion is added slowly;

(6) water, Part II water in the examples, in the amount of from 60 to 85 parts per hundred of the final compsition of the microemulsion is added slowly such that the total amount of water added in steps (5) and (6) ranges between 60 and 90 parts per hundred of the final composition of the microemulsion; and (7) adding an amount of an acid such that the final pH of the microemulsion is between about 4 and 7. Between steps (6) and (7) optional ingredients such as biocides or other additives may be added to the microemulsion.

A(3) contains at least one surfactant, wherein at least one of the surfactants is insoluble in the silicone of A(1), said surfactant hereinafter referred to as the primary surfactant. Other optional surfactants are referred to as secondary surfactants.

The surfactant or blend of surfactants has a hydrophilic-lipophilic balance value of from about 10 to about 16, preferably from about 12 to about 16, and most preferably from about 13 to about 14. The preferred hydrophilic-lipophilic balance value may vary as a consequence of increasing the level of volatile silicone in the microemulsifiable silicone.

The primary surfactant may be cationic, anionic, nonionic or amphoteric in nature. Examples of such surfactants are disclosed in U.S. Pat.No. 4,620,878 to Gee which is hereby incorporated by reference. Generally, nonionic surfactants are preferred for use in the instant invention.

Surfactants useful as the primary surfactant in the instant invention include the sorbitan esters of fatty acids having 10 to 22 carbon atoms; polyoxyethylene sorbitan esters of $C_{10}$ to $C_{22}$ fatty acids having up to 95% ethylene oxide; polyoxyethylene sorbitol esters of $C_{10}$ to $C_{22}$ fatty acids, polyoxyethylene derivatives of fatty phenols having 6 to 20 carbon atoms up to 95% ethylene oxide; fatty amino and amido betaines having 10 to 22 carbon atoms, and polyethylene condensates of $C_{10}$ to $C_{22}$ fatty acids or fatty alcohols having up to 95% ethylene oxide.

Preferred primary surfactants for the practice of the instant invention include, but are not limited to, the octylphenoxy polyethoxy ethanols, which are nonionic surfactants possessing varying amounts of ethylene oxide units and are available from Union Carbide Corporation under the general TRITON® trade name; trimethylnonyl polyethylene glycol ethers and polyethylene glycol ethers of linear 11–15 carbon atoms containing alcohols, available from Union Carbide Corporation under the general trade name TERGITOL®; the nonionic ethoxylated tridecyl ethers, available from Emery Industries under the trade name TRYCOL®; polyethoxylated quaternary ammonium salts and ethylene oxide condensation products of fatty amines available from Armak Company under the general trade names ETHOQUAD® and ETHOMEEN®, respectively, and alkoxylated siloxane surfactants containing ethylene oxide and/or propylene oxide groups. The surfactants listed herein above may be obtained from other suppliers under different trade names.

The preferred surfactants for use as the primary surfactant of the instant invention are the trimethylnonyl polyethylene glycol ethers and polyethylene glycol ethers of linear 11–15 carbon atom containing alcohols, available from Union Carbide Corporation under the trade name TERGITOL®. A preferred surfactant for use as the primary surfactant of the instant invention is a trimethylnonyl polyethylene glycol ether. The most preferred primary surfactant is N,N,N',N', N'-pentamethyl-N-tallow- 1,3-diammonium chloride.

The optional secondary surfactants may be anionic, cationic, nonionic, or amphoteric and may either be soluble or insoluble in the preferred amino functional silicone of (A)(1). Nonionic surfactants are preferred. Non-limiting examples of surfactants that are soluble in the amino functional silicone include the alkyl phenol ethoxylates.

Preferably, the optional secondary surfactant used in this invention is also insoluble in the silicone of A(1). The preferred surfactant for use as the secondary surfactant in the instant invention is a 70% aqueous solution of octylphenoxy polyethoxy (40) ethanol.

Preferably A(3) is a mixture of two nonionic surfactants, trimethyl nonyl polyethylene glycol ether (primary surfactant) and 70% aqueous solution of octylphenoxy polyethoxy (40) ethanol (secondary surfactant) being preferred, at a primary surfactant to secondary surfactant weight ratio of from about 1:2 to about 5:1, preferably from about 1:1 to about 3:1, and most preferably from about 9:2 to about 11:5.

The amount of A(3) is in the range of from about 1 to about 20, preferably from about 1 to about 10, and most preferably from about 1 to about 8, parts by weight per 100 parts by weight of the final croemulsion composition.

In steps (5) and (6) of the instant invention, the blend of silicones, surfactants and water is blended or mixed using an overhead stirrer or other suitable mixing equipment. The length of time necessary to form a homogeneous mixture or emulsion in this step will depend on mixing equipment parameters and can be determined by those skilled in the art without undue experimentation. Because the blend contains a volatile silicone, A(2), the temperature at which the microemulsion is formed must be carefully controlled to avoid loss of the volatile component. Thus step (4) is performed in a temperature range varying between 35° and 90° C., more preferably varying between 35° and 60° C., and most preferably varying between 35° and 45° C.

In step (7) the microemulsion is acidified to bring the pH of the emulsion into a range varying between 4 and 7, more preferably between 5 and 6.5, and most preferably between 5.5 and 6.5.

In order to change the pH of the reaction medium, it is necessary to consider the quantity of amino functional silicone or silicone present in the reaction mixture. The amount of acid needed to provide such pH values will depend on the amount of the amino functional silicone or silicone fluid (A)(1) and the amino content of the amino functional silicone fluid. For example, with the amino functional silicone fluid having an amino content of 0.6 milliequivalents per gram, the amount of acid sufficient to provide a pH within the desired range will be approximately 2.5 parts per weight per 100 parts per weight of the amino functional silicone fluid. With an amino functional silicone fluid having an amino content of 3.0 milliequivalents per gram, the weight of acid will be about 12.5 parts per weight per 100 parts per weight of the fluid. While the weights of acid necessary to achieve a given pH may vary depending on the molecular and equivalent weights of the acid chosen to control the pH, control of pH to the desired value is the primary purpose of the acid addition.

After step (6) a low molecular weight polyhydric alcohol or carbohydrate such as glycerin is optionally added to improve the clarity of the microemulsion in amounts ranging from 0.1 to about 20, more preferably from about 1 to about 7, and most preferably from about 3 to about 5 parts per hundred by weight of the final composition of the microemulsion.

EXPERIMENTAL

The procedure outlined in the detailed description of the invention was utilized to prepare the following non-limiting examples which are illustrative of the instant invention.

EXAMPLE 1

A silicone blend of an aminofunctional silicone and a volatile silicone, octamethylcyclotetrasiloxane, was prepared in a weight ratio of 9:1 respectively. This blend was employed to prepare a microemulsion having the following ratios of components:

20 parts by weight of the silicone blend, 5 parts by weight TERGITOL TMN-6®, 2.5 parts by weight TRITON-X 405®, 1.4 parts by weight water, Part I, 70.7 parts by weight water, Part II, 0.2 parts by weight DOWICIL 200®, a commercially available biocide available from DOW CHEMICAL CO., and 0.2 parts by weight glycerine.

The first attempt to prepare a microemulsion using this formulation produced an emulsion having a particle size range of from 50 to 150 nm. A second preparation produced a true clear microemulsion having a particle size ranging from 20 to 30 nm.

Example 2

A silicone blend of an aminofunctional silicone and a volatile silicone, octamethylcyclotetrasiloxane, was prepared in a weight ratio of 7.5:2.5 respectively. This blend was employed to prepare a microemulsion having the following ratios of components:

20 parts by weight of the silicone blend, 5 parts by weight TERGITOL TMN-6®, 2.5 parts by weight TRITON-X 405®, 1.4 parts by weight water, Part I, 67.0 parts by weight water, Part II, 0.2 parts by weight DOWICIL 200®, 0.2 parts by weight glycerine, and acetic acid in an amount sufficient to keep the pH in a range of from 5.5 to 6.0. This microemulsion was stable at room temperature, had a particle size ranging from 25 to 45 nm, was clear, i.e. transparent, and had a viscosity ranging between 10 and 25 centipoise at 25° C.

Example 3

A silicone blend of an aminofunctional silicone and a volatile silicone, octamethylcyclotetrasiloxane, was prepared in a weight ratio of 5:5 respectively. This blend was employed to prepare a microemulsion having the following ratios of components:

20 parts by weight of the silicone blend, 5 parts by weight TERGITOL TMN-6®, 2.5 parts by weight TRITON-X 405®, 1.4 parts by weight water, Part I, 67.9 parts by weight water, Part II, 0.2 parts by weight DOWICIL 200®, 3 parts by weight glycerine, and acetic acid in an amount sufficient to keep the pH in a range of from 5.5 to 6.0. This microemulsion was stable at room temperature, had a particle size ranging from 50 to 100 nm, and had a viscosity ranging between 10 and 25 centipoise at 25° C. Repeated attempts to lower the particle size range of this composition were unsuccessful. After several weeks of standing this emulsion separated into two distinct liquid phases. This emulsion was not stable over time.

Example 4

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 6 parts by weight TERGITOL TMN-6®, 1.5 parts by weight TRITON-X 405®, 1.4 parts by weight water, Part I, 70.7 parts by weight water, Part II, 0.2 parts by weight DOWICIL 200®, 0.2 parts by weight glycerine, and acetic acid in an amount sufficient to keep the pH in a range of from 5.5 to 6.0. This microemulsion was stable at room temperature, had a particle size ranging from 40 to 80 nm, had a viscosity ranging between 10 and 25 centipoise at 25° C., and a hydrophilic-lipophilic balance value of about 13. After several weeks of standing this emulsion separated into two distinct liquid phases. This emulsion was not stable over time.

Example 5

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 4 parts by weight TERGITOL TMN4®, 2 parts by weight TRITON-X 405®, 1.4 parts by weight water, Part I, 70.7 parts by weight water, Part II, 0.2 parts by weight DOWICIL 200®, 0.2 parts by weight glycerine, and acetic acid in an amount sufficient to keep the pH in a range of from 5.5 to 6.0. This microemulsion was stable at room temperature, had a particle size ranging from 50 to 100 nm, had a viscosity ranging between 10 and 25 centipoise at 250° C., and a hydrophilic-lipophilic balance value of about 13.8. After several weeks of standing this emulsion separated into two distinct liquid phases. This emulsion was not stable over time.

Example 6

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 4.5 parts by weight TERGITOL TMN-6®, 3 parts by weight TRITON-X 405®, 1.4 parts by weight water, Part I, 70.7 parts by weight water, Part II, 0.2 parts by weight DOWICIL 200®, 0.2 parts by weight glycerine, and acetic acid in an amount sufficient to keep the pH in a range of from 5.5 to 6.0. This microemulsion was not stable at room temperature, had an initial particle size ranging from 50 to 100 nm, had a viscosity ranging between 10 and 25 centipoise at 25° C., and a hydrophilic-lipophilic balance value of about 14.2. After several weeks of standing this emulsion separated into two distinct liquid phases. This emulsion was not stable over time.

Example 7

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 4 parts by weight TERGITOL TMN-6®, 3.5 parts by weight TRITON-X 405®, 1.4 parts by weight water, Part I, 70.7 parts by weight water, Part II, 0.2 parts by weight DOWICIL 200®, 0.2 parts by weight glycerine, and acetic acid in an amount sufficient to keep the pH in a range of from 5.5 to 6.0. This microemulsion was stable at room temperature, had a particle size ranging from 50 to 100 nm, had a viscosity ranging between 10 and 25 centipoise at 25° C., and a hydrophilic-lipophilic balance value of about 14.6. After several weeks of standing this emulsion separated into two distinct liquid phases. This emulsion was not stable over time.

Example 8

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 5.5 parts by weight TERGITOL TMN-6®, 2 parts by weight TRITON-X 405®, 1.4 parts by weight water, Part I, 67.9 parts by weight water, Part II, 0.2 parts by weight DOWICIL 200®, 3 parts by weight glycerine, and acetic acid in an amount sufficient to keep the pH in a range of from 5.5 to 6.0. This microemulsion was stable at room temperature, had a particle size ranging from 40 to 80 nm, had a viscosity ranging between 10 and 25 centipoise at 25° C., and a hydrophilic-lipophilic balance value of about 13.4. After several weeks of standing this emulsion separated into two distinct liquid phases. This emulsion was not stable over time.

Example 9

A silicone blend of an aminofunctional silicone and a volatile silicone, octamethylcyclotetrasiloxane, was prepared in a weight ratio of 7:3 respectively. This blend was employed to prepare a microemulsion having the following ratios of components:

20 parts by weight of the silicone blend, 5 parts by weight TERGITOL 15-S5®, 2.5 parts by weight TERGITOL 15-s40®, 1.4 parts by weight water, Part I, 67.9 parts by weight water, Part II, 0.2 parts by weight DOWICIL 200®, 3 parts by weight glycerine, and acetic acid in an amount sufficient to keep the pH in a range of from 5.5 to 6.0. This microemulsion was stable at room temperature, had a particle size ranging from 40 to 60 nm, had a viscosity ranging between 10 and 25 centipoise at 250° C., and a hydrophilic-lipophilic balance value of about 13.1. After several weeks of standing this emulsion separated into two distinct liquid phases.

Example 10

A silicone blend of an aminofunctional silicone and a volatile silicone, octamethylcyclotetrasiloxane, was prepared in a weight ratio of 7:3 respectively. This blend was employed to prepare a microemulsion having the following ratios of components:

20 parts by weight of the silicone blend, 5 parts by weight TERGITOL 15-S5®, 2.5 parts by weight TERGITOL 15-s-40®, 1.4 parts by weight water, Part I, 70.7 parts by weight water, Part II, 0.2 parts by weight DOWICIL 200®, 5 parts by weight glycerine, and acetic acid in an amount sufficient to keep the pH in a range of from 5.5 to 6.0. This microemulsion was stable at room temperature, had a particle size above 50 nm, and had a viscosity ranging between 10 and 25 centipoise at 25° C.

Example 11

A silicone blend of an aminofunctional silicone and a volatile silicone, octamethylcyclotetrasiloxane, was prepared in a weight ratio of 7:3 respectively. This blend was employed to prepare a microemulsion having the following ratios of components:

20 parts by weight of the silicone blend, 5 parts by weight TERGITOL TMN-6®, 2.5 parts by weight TRITON-X 405®, 1.4 parts by weight water, Part I, 65.9 parts by weight water, Part II, 0.2 parts by weight DOWICIL 200®, 5 parts by weight glycerine, and acetic acid in an amount sufficient to keep the pH in a range of from 5.5 to 6.0. This microemulsion was stable at room temperature, had a particle size ranging from 15 to 40 nm, had a viscosity ranging between 10 and 25 centipoise at 25° C., and a hydrophilic-lipophilic balance value of about 13.8.

Example 12

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 6 parts by weight TERGITOL TMN-6®, 3 parts by weight TRITON-X 405®, 1.4 parts by weight water, Part I, 70.7 parts by weight water, Part II, 0.2 parts by weight DOWICIL 200®, 5 parts by weight glycerine, and acetic acid in an amount sufficient to keep the pH in a range of from 5.5 to 6.0. This microemulsion was stable at room temperature, had a particle size ranging from 20 to 35 nm, had a viscosity significantly higher than previous preparations, and a hydrophilic-lipophilic balance value of about 13.8.

Example 13

A silicone blend of an aminofunctional silicone and a volatile silicone, octamethylcyclotetrasiloxane, was prepared in a weight ratio of 6.5:3.5 respectively. This blend was employed to prepare a microemulsion having the following ratios of components:

20 parts by weight of the silicone blend, 5 parts by weight TERGITOL 15-S5®, 2.5parts by weight TERGITOL 15-s40®, 1.4 parts by weight water, Part I, 65.9 parts by weight water, Part II, 0.2 parts by weight DOWICIL 200®, 5 parts by weight glycerine, and acetic acid in an amount sufficient to keep the pH in a range of from 5.5 to 6.0. This microemulsion was stable at room temperature, had a particle size ranging from 25 to 35 nm, had a viscosity that was significantly higher than previous preparations, and a hydrophilic-lipophilic balance value of about 13.1.

Having described the invention, we claim:

1. A translucent oil-in-water microemulsion comprising:

(a) a microemulsifiable silicone comprising an aminofunctional silicone of the formula:

$(CH_3)_3SiO((CH_3)(C_3H_6NHC_2H_4NH_2)SiO)_x((CH_3)_2SiO)_ySi(CH_3)_3$ wherein x is a number in the range of from 1 to about 20 and y is a number in the range from about 20 to about 800;

(b) a volatile silicone,

$R_dR_eSiO)_n$ where $R_d$ and $R_e$ may be identical or different alkyl radicals having from 1 to 4 carbon atoms and where n is an integer varying from between about 3 to about 7;

(c) a surfactant, and (d) water wherein the ASTM D871 haze number ranges from 0 to about 150.

2. A process for preparing a microemulsion comprising:

(a) preparing a blend of silicones comprising:

(i) a microemulsifiable silicone of the formula:

$$M(R_aQ_bSiO_{(4-a-b)/2})_x(R_cSiO_{(4-c)/2})_yM$$

wherein R is a hydrocarbon or hydrocarbon radical having from 1 to about 6 carbon atoms, Q is a polar radical having the formula—$R^1HZ$, wherein $R^1$ is a divalent linking group comprised of carbon and hydrogen atoms; carbon, hydrogen and oxygen atoms, or carbon, hydrogen and sulfur atoms; and Z is a radical selected from the group consisting of hydrogen atoms, alkyl radicals having from 1 to 4 carbon atoms, and —$CH_2CH_2NH_2$ radicals; a ranges from about 1 to about 2, b ranges from about 1 to about 3 such that a+b is less than or equal to 3, and c is a number in the range of from about 1 to about 3; and x is a number in the range of from 1 to about 20 and y is a number in the range from about 20 to about 800, and M is a silicone endstopping group; and (ii) a volatile silicone of the formula:

$$(R_dR_eSiO)_n$$

where $R_d$ and $R_e$ may be identical or different alkyl radicals having from 1 to 4 carbon atoms and where n is an integer varying from between about 3 to about 7; and (b) adding to said blend a surfactant;

(c) raising the temperature of the silicone surfactant blend to a range of from about 35° to 90° C.;

(d) adding Part I water in an amount ranging from about 0.50 to about 5.00 parts per hundred based on the final ccomposition of the emulsion;

(e) adding Part II water in an amount ranging from about 60 to about 5 to about 85 parts per hundred based on the final composition of the emulsion thereby forming a microemulsion; and (f) adding an acid in an amount sufficient to adjust the pH of the microemulsion to a range of from about 4 to about 7.

3. The process of claim 2 wherein the microemulsifiable silicone is selected from the group of silicones of the formula:

$$(CH_3)_3SiO((CH_3)(C_3H_6NHC_2H_4NH_2)SiO)_x((CH_3)_2SiO)_ySi(CH_3)_3$$

wherein x is a number in the range of from 1 to about 20, and y is a number in the range from about 20 to about 800.

4. The process of claim 2, where the temperature is controlled in a range of from about 35° to 45° C.

5. The process of claim 4 where the pH is controlled in a range of from about 5.5 to about 6, having an ASTM D871 haze number of about 150 or less.

* * * * *